United States Patent [19]

Pillsbury

[11] Patent Number: 4,700,011
[45] Date of Patent: Oct. 13, 1987

[54] METHODS FOR THE PRODUCTION AND PURIFICATION OF DI (NITROPHENYL) ETHERS

[75] Inventor: Dale G. Pillsbury, Elburn, Ill.

[73] Assignee: Amoco Corporation, Chicago, Ill.

[21] Appl. No.: 782,229

[22] Filed: Sep. 30, 1985

[51] Int. Cl.$^4$ .................. C07C 43/275; C07C 79/35
[52] U.S. Cl. .................................................. 568/585
[58] Field of Search ...................................... 568/585

[56] References Cited

U.S. PATENT DOCUMENTS

| 3,032,594 | 12/1960 | Towle | 260/612 |
| 3,192,263 | 6/1965 | Splegler | 260/571 |
| 3,387,041 | 6/1968 | Oscar | 260/612 |
| 3,422,154 | 1/1969 | Lauclus | 260/612 |
| 3,442,956 | 5/1969 | Sheets | 260/612 |
| 3,634,519 | 1/1972 | Bentz et al. | 260/612 R |

OTHER PUBLICATIONS

Morton, Laboratory Technique in Organic Chemistry (1938).

Primary Examiner—Werren B. Lone
Attorney, Agent, or Firm—Maria Parrish Tungol; William H. Magidson; Ralph C. Medhurst

[57] ABSTRACT

Di(nitrophenyl) ethers are prepared by the reaction of a halogeno-nitrophenyl compound with a base wherein the water in the reaction system is removed during the reaction. The reaction can be advantageously carried out at two different temperatures. The use of a molar excess of the halogeno-nitrophenyl compound improves the yield of di(nitrophenyl) ether. Crude di(nitrophenyl) ether is purified by extraction into a non-aqueous solvent using a dual temperature method to maintain the ether in the liquid phase.

35 Claims, No Drawings

METHODS FOR THE PRODUCTION AND PURIFICATION OF DI (NITROPHENYL) ETHERS

BACKGROUND OF THE INVENTION

This invention relates to processes for producing di(nitrophenyl) ethers and the purification of crude di(nitrophenyl) ether reaction products. More particularly, di(nitrophenyl) ethers are prepared by the reaction of a halogeno-nitrophenyl compound with a base wherein the water in the reaction system is removed during the reaction. The use of two different temperatures during the reaction is advantageous. The yield of di(nitrophenyl) ether is improved by the use of a molar excess of halogeno-nitrophenyl compound. Purification is performed by extraction into a non-aqueous solvent using a dual temperature method.

Di(nitrophenyl) ethers have been prepared from the reaction of alkali metal nitrophenolates and certain halogeno-nitrobenzenes by the Williamson synthesis. Di(nitrophenyl) ethers may be subsequently hydrogenated to form diamino-diphenyl ethers. The diamino-diphenyl ethers are useful as bifunctional cross-linking network-extending agents for various polymers. In particular, bis(para-nitrophenyl)ether is hydrogenated to oxybis(aniline) which in turn is used as a monomer to produce high molecular weight polymers, e.g., amide-imide terpolymers.

Diamino-diphenyl ethers have been prepared by the condensation of halogeno-mononitrobenzene with an alkali metal nitrophenate in a solvent such as dimethyl-acetamide by Spiegler in U.S. Pat. No. 3,192,263. However, there are several disadvantages in preparing the ether by using an alkali metal nitrophenate as a starting material. First, the nitrophenate is prepared separately by reaction of a halogeno-nitrobenzene and a base. After the reaction, the unreacted halogeno-nitrobenzene is removed some means, e.g., steam distillation. Such a process of removal can be extremely hazardous since the nitrophenate may explode at high temperatures.

A process which involves the in situ formation of the alkali metal nitrophenate by the reaction of a base with a halogeno-nitrobenzene has been disclosed by Bentz et al. in U.S. Pat. No. 3,634,519. The reference teaches the production of 4,4'-dinitro-diphenyl ethers by the condensation of a 1-halo-4-nitrophenyl compound with an aqueous solution of an alkali metal hydroxide wherein the molar ratio of phenyl compound to alkali metal hydroxide is between 1:1 and 1:1.1, i.e., a slight excess of hydroxide is used in the reaction.

The object of this invention is to provide improved methods of conducting the reaction of a base with a halogeno-nitrophenyl compound which avoids the problems associated with handling the nitrophenate and significantly improves the selectivity to and yield of di(nitrophenyl) ether with reduced formation of undesirable by-products. A further object of this invention is to provide a method of purifying crude di(nitrophenyl) ether reaction products by an extraction method which reduces the amount of impurities in the final product and avoids costly and inconvenient solids handling operations.

SUMMARY OF THE INVENTION

Di(nitrophenyl) ethers are prepared by the reaction of a halogeno-nitrophenyl compound with a base wherein the water in the reaction system is removed during the reaction. The reaction can be advantageously carried out at two different temperatures. The use of a molar excess of the halogeno-nitrophenyl compound improves the yield of di(nitrophenyl) ether. Crude di(nitrophenyl) ether can be purified by extraction into a non-aqueous solvent using a dual temperature method to maintain the ether in the liquid phase.

DESCRIPTION OF THE INVENTION

This invention is an improved process of producing di(nitrophenyl) ethers by the reaction of a base with a halogeno-nitrophenyl compound wherein water is removed from the reaction system during the reaction. The formation of undesired by-products is further reduced by using two different temperatures during the reaction. It has also been discovered that the selectivity to and yield of di(nitrophenyl) ether is improved when an excess of the halogeno-nitrophenyl compound over the amount of base is used in the reaction. Further, this invention involves a method of purifying crude di(nitrophenyl) ether by extraction into a non-aqueous solvent using a dual temperature technique to maintain the ether in the liquid phase.

The reaction of a halogeno-nitrophenyl compound with a base can be described as a partial hydrolysis-etherification reaction wherein a nitrophenoxide ion is formed by the reaction of the base with the halogeno-nitrophenyl compound. The ion then reacts with any halogeno-nitrophenyl compound present to form the di(nitrophenyl) ether. Water and the halogen salt of the base are also produced in the reaction. Our studies have shown that water has a deleterious effect on the rate of etherification.

Halogeno-nitrophenyl compounds which can be used in my process include nitrobenzene compounds which contain at least one halogen substituent. Examples of such compounds include o-chloronitrobenzene, p-chloronitrobenzene, 2,5-2,3- and 3,4-dichloronitrobenzene, 4-chloro-3-nitrotoluene, and o- or p-chloronitrobenzenes containing a methyl group in any other position, 2-chloro-5-ethylnitrobenzene, 5-chloro-2-nitroanisol, 4-chloro-2,5,-dimethylnitrobenzene, and 4-chloro-3-nitrophenetol. The corresponding bromonitrobenzenes and fluoro-nitrobenzenes such as para-fluoro-nitrobenzene can also be used in my process. Para-chloro-nitrobenzene is a preferred reactant for the production of bis(para-nitrophenyl) ether.

Suitable bases include those basic compounds which are capable of reacting with the halogeno-nitrophenyl compound to form the nitrophenoxide ion. Examples of such bases include both organic and inorganic bases. Examples of organic bases are quaternary ammonium hydroxides such as trimethylbenzyl ammonium hydroxide. Inorganic bases include alkali metal or alkali earth metal hydroxides, carbonates, bicarbonates, nitrites and disodium phosphate. The bases are preferably added to the reaction mixture as concentrated aqueous solutions. The use of the concentrated solutions minimizes the addition of water to the reaction system. Alkali metal hydroxides can be used as 45–50% aqueous solutions. Sodium hydroxide is the preferred base because a 50% aqueous solution contains more moles of base than a 45–50% aqueous solution of potassium hydroxide and is less expensive.

The reaction of this invention is conducted in a reaction medium comprising an organic solvent capable of dissolving the halogeno-nitrophenyl compound. Useful organic solvents include aliphatic amides, such as those disclosed in U.S. Pat. Nos. 3,192,263 and 3,387,041, both incorporated herein by reference, organic sulfones such as those disclosed in U.S. Pat. No. 3,422,154, incorporated herein by reference, and sulfoxides such as diethyl sulfoxide and dimethyl sulfoxide. Other suitable organic solvents include base stable, high boiling polyethers such as dialkyl ethers of polyethylene glycols and macrocyclic ethers such as crown ethers. Dimethyl sulfoxide is the preferred solvent because of its low reactivity in strongly basic solutions, availability, and cost. Its boiling point is high enough so that it does not evaporate during the reaction yet low enough for convenient solvent recovery after the reaction. When the organic solvent is immiscible with the aqueous solution of the base, a high degree of agitation favors the partial hydrolysis stage of the reaction. As explained below, the reaction medium can also contain an entrainer which may or may not be capable of dissolving the halogeno-nitrophenyl compound.

According to the process of this invention, water is removed from the reaction system during the addition of the base to the halogeno-nitrophenol compound and throughout the reaction period. The water formed by the reaction is removed in addition to any water which was present in the initial reactants. The removal of water from the reaction system appears to increase the rate of reaction of the halogeno-nitrophenyl compound and the nitrophenoxide ion. The rate of etherification observed in the absence of water is typically twice the rate observed in the presence of water. The removal of water from the reaction system resulted in improved yield and less by-product formation when compared to a process in which the water formed during the reaction was not removed.

The water can be removed continuously or in increments by various known means. It can be removed by simple distillation, distillation under partial vacuum, or with an inert gas (e.g., $N_2$) sparge. Incremental removal can be performed by distilling the water out at predetermined intervals and permitting the reaction to reflux the rest of the time. It is preferred to remove the water continuously during the reaction to maximize the efficiency of the etherification reaction. A convenient method of continous removal is the heteroazeotropic distillation of water from the reaction system with a suitable hydrocarbon entrainer which can be recycled to the reaction mixture. The entrainer is added to the reaction mixture prior to reaction. Suitable entrainers are hydrocarbons which are liquid at room temperature and have boiling points less than about 200° C. Mixtures of xylenes have been found to be very effective as entrainers because of their advantageous boiling points. Examples of other entrainers include nonane and decahydronaphthalene. The amount of entrainer required to form a heteroazeotrope with water and for later recirculation depends upon the size of the equipment and is readily determined by known methods by one skilled in the art. Although the hydrocarbon entrainers can act as solvents for the reactants, it is preferred that the reaction medium comprise non-hydrocarbon organic solvents capable of dissolving the halogeno-nitrophenyl compound. The instant method of water removal is advantageous because the heat absorption by the azeotroping water tends to offset any exotherm associated with the partial hydrolysis step thereby facilitating temperature control of the reaction.

As explained below, the process can be run isothermally or at different temperatures. When the reaction is run isothermally, the reaction temperature must be maintained below about 170° C. to minimize the formation of polar by-products. Preferably, the reaction is conducted in the temperature range of about 150° to 160° C., most preferably around 150° C. The time required for the reaction depends upon the temperature chosen and, in general, is in excess of 4 hours in the isothermal method. Water is continuously removed from the reaction system during the addition of the base and throughout the reaction period. When instant process is conducted in a single temperature range it is preferred that a molar excess of halogeno-nitrophenyl compound be used to maximize yield and selectivity.

Advantageously, the process of the invention can be conducted at two different temperatures. The base is added while the reaction mixture is maintained within a first temperature range of about 60° to less than 150° C. Then, the reaction temperature is raised to a higher temperature range of about 150° to 170° C. where it is maintained during the rest of the reaction period. It has been discovered that the use of two different temperatures during the reaction decreases formation of undesired by-products when compared with the use of a single temperature range. When two temperatures are used, the total residence time required for good conversion is maintained within reasonable limits. The lower temperature is that temperature at which the partial hydrolysis reaction proceeds at an acceptable rate with minimum by-product formation. The higher temperature is that temperature at which etherification proceeds at an acceptable rate without decomposition of reagents, solvent, or reaction product. In particular, a lower temperature range of about 115° to 130° C. is preferred since it promotes the partial hydrolysis reaction. A higher temperature range of about 160° to 170° C. is preferred since it increases the rate of etherification while minimizing by-product formation.

In the two temperature method, the reaction mixture is maintained at the lower temperature range for about 1 hour and at the higher temperature range for about 1 to 2 hours. Longer residence time at the higher range results in an improvement in conversion and selectivity while the level of by-product formation remains essentially constant. As before, water is removed during the addition of the base and throughout the reaction period. Water removal can be incremental or continuous. Continuous removal of water is preferred.

Another aspect of this invention which improves the selectivity to and yield of di(nitrophenyl) ether is the molar ratio of the halogeno-nitrophenyl compound to base. It has been found that the use of an excess of halogeno-nitrophenyl compound results in a higher conversion of said compound to the ether and minimizes the amount of unreacted intermediate, i.e., para-nitrophenoxide which is difficult to recover and is a known toxin. In particular, it has been discovered that the use of a molar ratio of halogeno-nitrophenyl compound to base which is greater than 1:1, e.g., 1.01:1, preferably at least 1.15:1, gives both higher conversion and selectivity to the di(nitrophenyl) ether when compared to the equimolar ratio such as that taught by Bentz et al. The advantages of using instant molar ratio are observed in both the isothermal and dual temperature methods of this invention. Most of the unreacted excess halogen-nitrophenyl compound can be recovered together with the organic solvent in a post-reaction stripping procedure.

The improvement in yield and lower by-product formation in instant invention is unobvious over the process of Bentz et al. since the reference does not teach or suggest the removal of water during the reaction. In contrast, Bentz et al. conducted their process under reflux. Also, the reference does not teach or suggest the use of a molar excess of halogeno-nitrophenyl compound over base. Instead, it teaches the use of an excess of base.

When the reaction is complete, the solvent and unreacted halogeno-nitrophenyl compound can be removed from the reaction mixture by vacuum stripping. Most of the solvent and unreacted halogeno-nitrophenyl compound are stripped at about 100 mm Hg under simple distillation conditions. The stripping stage is finished at about 35 to 40 mm Hg for maximum recovery of the halogeno-nitrophenyl compound. The vapor volume under these conditions is low and a simple one or two stage steam ejector can be used, thus eliminating the need for an expensive vacuum system. Alternatively, the solvent and unreacted hydrocarbon can be removed by $N_2$ sparging.

The hot stripped partial hydrolysis-etherification reaction mixture is a pumpable slurry of melted crude di(nitrophenyl) ether, dissolved and undissolved organic by-products, and finely dispersed halide salt of the base, e.g., sodium or potassium chloride. This reaction mixture can be quenched by cold water and the crude solid product can be thoroughly washed with hot water prior to subsequent hydrogenation. The water-quenched, water-washed di(nitrophenyl) ether is readily hydrogenated to diamino-diphenyl ether if high enough pressure is used. However, because of residual by-products in the water-washed ether, it was found that the hydrogenation product, diamino-diphenyl ether, had to be purified by two stages of crystallization to obtain an acceptable product. Three instances of solids handling in the production of the di(nitrophenyl) ether and the following hydrogenation to the diamino-diphenyl ether present difficult manufacturing problems, e.g., the amount and size of equipment required, transportation of the solid material, possible exposure of personnel to toxic materials and the handling of damp or dissolved diamino-diphenyl ether which is very prone to oxidation.

It has been found that the melting points of di(nitrophenyl) ethers and their temperature dependent solubility in hydrocarbon solvents permit the separation and purification of the ether from the crude reaction product under conditions which avoid costly and inconvenient solids handling operations. Such a method of purification has produced di(nitrophenyl) ether which contained about half the amount of by-products contained in the ether obtained by a water-wash method and hydrogenated more readily to the diamino-diphenyl ether. The resulting hydrogenation product was isolated by a single stage of crystallization and was of similar quality to the product isolated by two stages of crystallization required when using the water-wash method. A product which was extracted into 177° C. decahydronaphthalene was found to have a greater degree of hydrogenation than a product which was only washed with cold water. The preferred di(nitrophenyl) ether used in my method of separation and purification is bis(paranitrophenyl) ether which can be subsequently hydrogenated to form oxybis(aniline).

This method of separation and purification can be applied to any crude reaction product containing a di(nitrophenyl) ether. It can be applied in any process for the production of di(nitrophenyl) ether in which the reaction product is apt to be contaminated with undesired by-products or intermediates such as the para-nitrophenoxide salt whether pre-formed or formed in situ. These residual phenolic salts are insoluble in the extracting solvents used in this method. Examples of the crude reaction products which can be purified by instant process include the crude products of the processes disclosed in U.S. Pat. Nos. 3,192,263, 3,387,041, 3,422,154, 3,634,518. The instant method can also be used to recover the corresponding di(nitrophenyl) thioethers such as bis(para-nitrophenyl) thioether.

Crude water-quenched di(nitrophenyl) ether can be dissolved in hot extracting solvent leaving the more polar by-products undissolved. When the hot solvent solution is cooled to a lower temperature, two liquid layers are formed, the lower of which contains a high percentage of molten ether. The ether-containing layer can then be separated from the composition in liquid form. The extraction method of this invention is preferably carried out in the substantial absence of water. Hence, the extraction can be carried out in the partial hydrolysis-etherification reactor. The di(nitrophenyl) ether should not be adversely affected by the absence of water since the ether is extracted as a melt under conditions which are essentially the same as those in the etherification stage of the reaction. In the absence of water, the polar insoluble organic by-products, which tend to be tarry, are dispersed on the halide salt. Concentration of solid by-products in one place facilitates disposal.

Suitable extracting solvents for instant process include aliphatic and aromatic hydrocarbons, especially decahydronaphthalene, dodecane, decane or mixtures thereof. Decane is the preferred solvent for the purification of bis(para-nitrophenyl) ether because it is the the more discriminating solvent for this ether. Other less expensive hydrocarbons or mixtures thereof can be used in my process. Once the extracting solvent has been selected, the temperature ranges for dissolution of the di(nitrophenyl) ether and the following cooling step can be determined. The solvent should be heated so that an appreciable amount of the di(nitrophenyl) ether is dissolved. The ether-containing solvent solution is then cooled to a temperature range at which two separate liquid layers are formed while the di(nitrophenyl) ether remains in the liquid phase. The lower temperature can be readily determined for each ether-solvent combination, i.e., that temperature at which the di(nitrophenyl) ether does not precipitate out of solution in a particular extracting solvent. When hydrocarbon solvents are used to extract bis(para-nitrophenyl) ether, said ether is dissolved therein at a temperature between about 150° to 250° C. The solvent solution is then cooled to a temperature in the range of about 135° to 140° C.

It is possible to add a polar solvent such as ethanol to the hot hydrocarbon solution containing the di(nitrophenyl) ether. When the polar solvent has low solubility in hot hydrocarbon and good dissolving power for the ether, partitioning of the ether will occur. If the solvent, e.g., aqueous ethanol, is useful in the subsequent hydrogenation reaction, the resulting solution could be used directly as a feed for the hydrogenation reaction.

The following examples are given for the purpose of further illustrating the present invention and are not intended in any way to limit the scope of the invention. The methods of this invention can be conducted as a batch process or as a contiuous process with appropriate modifications which can be readily determined by one skilled in the art.

EXAMPLE 1

Sixteen hundred ml of a 3.09M solution of para-chloro-nitrobenzene dissolved in dimethyl sulfoxide and 50 ml of nonane were placed in a 3 liter glass resin kettle reactor. The mixture was heated to a temperature of about 150° C. and 345 ml of a 14.28M solution of KOH (molar ratio of para-chloro-nitrobenzene:-KOH=1:1) were pumped into reactor.

Water was continuously removed from the reaction system through a Vigreux column connected to a Dean-Stark trap. The water was then moved from the trap to a collector vessel.

The reaction mixture was stirred vigorously and after 4.5 hours, the reaction mixture was analyzed by gas chromatography. The yield of bis (para nitrophenyl) ether (BNPE) was calculated as follows:

$$yield = \frac{actual\ weight\ of\ BNPE}{theoretical\ maximum\ weight\ of\ BNPE} \times 100$$

wherein actual weight of $BNPE =$ $$\frac{weight\ of\ BNPE\ in\ product\ by\ gas\ chromotography}{100} \times total\ weight\ of\ product$$

and theoretical maximum weight of $BNPE =$ $$\frac{liters\ KOH \times molarity\ KOH}{2} \times 260.2\ g/mole\ BNPE$$

Bis(para-nitrophenyl) ether was obtained in a yield of 55.5% based on para-chloro-nitrobenzene. The polar by-product content was 5.0% by weight of the final product.

COMPARATIVE EXAMPLE

A process which was essentially the same as that of Bentz et al. in U.S. Pat. No. 3,634,519 was performed to demonstrate the advantages of instant processes. 236.25 grams of para-chloro-nitrobenzene and 750 ml of dimethyl sulfoxide were added to a 3 liter glass resin kettle. The reaction mixture was heated to 170° C. and a solution of 125.55 grams of 89.4% KOH (molar ratio of 1:1) dissolved in 87 ml of water was added dropwise to the mixture. A total of 103.5 ml of the KOH solution was added. The mixture was stirred under reflux for 4 hours. The reaction mixture was quenched by pouring it into 3 1 of ice water. The solid product was suction filtered overnight. The yield of bis(para-nitrophenyl) ether based on the KOH or para-chloro-nitrobenzene was 36.9%. The amount of undesirable by-products in the reaction product was 15.1% by weight.

EXAMPLE 2

This example illustrates the advantages of using two different temperatures during the reaction.

A 1220 ml sample of a 3.08M solution of para-chloronitrobenzene dissolved in dimethyl sulfoxide and 50 ml of decahydronaphthalene were placed in a 3 liter glass resin kettle reactor. The mixture was heated to a temperature of about 115° C. and 259 ml of a 14.28M solution of KOH (molar ratio of 1:1) were pumped into the reactor while the temperature was raised to about 130° C. over a period of 40 minutes. Water was continuously removed from the reaction system through a Vigreux column connected to a Dean-Stark trap as in Example 1.

When the KOH addition was completed, the reaction mixture was heated to 170° C. After about 2.5 hours, the reaction mixture was stripped on a rotary evaporator at 100 mm Hg until the temperature of the mixture was 170° C. The stripped material was quenched in 2 liters of nitrogen-spared distilled water then filtered. It was washed in 6 liters of distilled water and filtered overnight. Bis(para-nitrophenyl) ether was obtained in a yield of 84.5% based on para-chloro-nitrobenzene. The polar by-product content was 1.9% by weight of the final product.

EXAMPLE 3

A sample of 669.8 g of para-chloro-nitrobenzene (a 15% molar excess) dissolved in 855.9 g of dimethyl sulfoxide and 50 ml of decahydronaphthalene were placed in a 3 liter glass resin kettle reactor. The mixture was heated to a temperature of about 116° C. and 264 ml of a 14.01M solution of KOH were poured into the reactor while the temperature was raised to about 130° C. over a period of 40 minutes. Water was continuously removed from the reaction system through a Vigreux column connected to a Dean-Stark trap as in Example 1.

When the KOH addition was completed, the reaction mixture was heated to 170° C. After about 2.3 hours, the reaction mixture was stripped in a rotary evaporator. It was held at 110 mm Hg until the inside temperature reached 170° C., then the pressure was adjusted to 37 mm Hg and the temperature was raised again to 170° C. The cold finger containing dry ice was inserted as in Example 1 and the bath temperature was held at 175° C. at a pressure of 37 mm Hg for 1.5 hours. The stripped material was quenched in 2 liters ice/3 liters water with stirring, the suction filtered overnight. After four washings on the filter with about 2 liters of 80° C. water, it was suction filtered to dryness. Bis(paranitrophenyl) ether was obtained in a yield of 84.1% based on KOH and 73.8% based on -para-chloro-nitrobenzene. The polar by-product content was 2.5% by weight of the final product.

EXAMPLE 4

A 669.7 g sample of para-chloro-nitrobenzene (a 15% molar excess) dissolved in 767 ml of dimethyl sulfoxide and 50 ml of decahydronaphthalene was placed in a 3 liter glass resin kettle reactor. The mixture was heated to a temperature of about 117° C. and 192 ml of a 19.29M solution of NaOH were pumped into the reactor while the temperature was raised to about 134° C. over a period of 35 minutes. Water was continuously removed from the reaction system through a Vigreux column connected to a Dean-Stark trap as in Example 1.

When the NaOH addition was completed, the reaction mixture was heated to 170° C. After about 2.4 hours, the reaction mixture was stripped as in Example 3. The stripped material was quenched in 5 liters of ice water and stirred for about 1 hour. It was filtered to dryness overnight, then crushed and sieved through a 20 mesh screen. It was stirred in 50° C. water for 1 hour then filtered. After four washings on the filter with about 1 liter of 80° C. water, it was filtered dry. Bis(-para-nitrophenyl) ether was obtained in a yield of 81.5% based on NaOH. The by-product content was 9.96% by weight of the final product.

EXAMPLE 5

The product of Example 2 was extracted with refluxing decane in a liquid-liquid extractor for several hours. Molten by-product remained in the bottom. The refluxing liquid containing the extracted bis(para-nitrophenyl) ether was cooled until a liquid layer became apparent at the bottom of the flask. This layer was drawn off in a pipette and cooled until a solid was formed. This solid was washed with hexane, crushed, washed again with hexane, and dried. The resulting yellow solid was then hydrogenated to oxybis(aniline) by the following procedure. A sample of 150 grams of the bis(para-nitrophenyl) ether, 6.42 grams of a Raney Nickel catalyst and 600 ml of 95% ethanol were charged to a one liter stirred autoclave. The closed reactor was purged with hydrogen, heated to 161° C. and pressurized to 1,500 pounds of pressure. The hydrogenation was conducted for 40 minutes. The reaction product mixture was slowly transferred under nitrogen pressure to a collector until overnight. The unit was opened under nitrogen and the product was filtered to dryness.

The yield of oxybis(aniline) was 84.9% based on the BNPE in the feed with a melting point of 187°–190.5° C.

EXAMPLE 6

A sample of crude bis(para-nitrophenyl) ether prepared by the process of this invention was washed with cold water. 5.00 grams of this sample was charged to an autoclave together with 0.03 grams of 9% Pd on charcoal and 20 ml of 95% ethanol. The mixture was shaken at 159°–163° C. at 800 pounds of pressure of hydrogen for 30 minutes. The product was cooled, vented, opened under nitrogen, and analyzed by gas chromatography. The yield of oxybis (aniline) was only 7.0% based on available bis(para-nitrophenyl) ether.

EXAMPLE 7

The procedure of Example 6 was repeated using a sample of bis(para-nitrophenyl) ether which was separated from the crude product by extraction into 177° C. decahydronaphthalene. The yield of oxybis (aniline) was 26.7%.

What is claimed is:

1. A process of producing a di(nitrophenyl) ether comprising reacting a halogeno-nitrophenyl compound with a base wherein the molar ratio of halogeno-nitro phenyl compound to base is at least 1:1 and the water in the reaction system is removed during said reaction.

2. A process according to claim 1 wherein the halogeno-nitrophenyl compound comprises a chloro-, bromo-, or fluoro-nitrophenyl compound or mixtures thereof.

3. A process according to claim 1 wherein the halogeno-nitrophenyl compound comprises para-chloro-nitrobenzene.

4. A process according to claim 1 wherein said base comprises an alkali metal hydroxide.

5. A process according to claim 1 wherein the molar ratio of halogeno-nitrophenyl compound to base is at least 1.15:1.

6. A process according to claim 1 wherein a hydrocarbon entrainer is added to the reaction mixture and the water is continously removed from the reaction system by the heteroazeotropic distillation of water with said entrainer which is comprised of a hydrocarbon which is liquid at room temperature and has a boiling point less than about 200° C.

7. A process according to claim 1 wherein the reaction is conducted at a temperature less than 170° C.

8. A process according to claim 1 wherein the reaction is conducted in a reaction medium comprising an organic solvent capable of dissolving the halogeno-nitrophenyl compound.

9. A process according to claim 8 wherein the reaction is conducted in dimethylsulfoxide as said solvent.

10. A process according to claim 8 wherein, after the reaction is completed, the di(nitrophenyl) ether is recovered from the reaction product mixture by:
    (a) separating said solvent and unreacted halogeno-nitrophenyl compound from said mixture by vacuum distillation,
    (b) treating the residue of step (a) with a non-aqueous extracting solvent for the di(nitrophenyl) ether at temperature at which said ether dissolves in said extracting solvent,
    (c) cooling the resulting composition to a temperature at which two separate liquid layers are formed, and (d) separating the ether containing layer from the resulting two-layer composition.

11. A process according to claim 10 wherein step (b) is performed at a temperature in the range of about 150° to 250° C.

12. A process according to claim 11 wherein the composition from step (b) is cooled to a temperature in the range of about 135° to 140° C.

13. A process according to claim 10 wherein said extracting solvent in step (b) is an aliphatic or aromatic hydrocarbon or mixtures thereof.

14. A process according to claim 13 wherein said solvent is selected from the group consisting of decahydronaphthalene, dodecane and decane.

15. A process according to claim 14 wherein said solvent is decane.

16. A process of producing a di(nitrophenyl) ether which comprises: (a) combining a base and a halogeno-nitrophenyl compound at a temperature below about 150° C., (b) subsequently raising the temperature of the reaction mixture to a temperature above about 150° C. at which etherification occurs, and (c) removing water from the reaction system during steps (a) and (b), wherein the molar ratio of halogeno-nitrophenyl compound to base is at least 1:1 and the temperature of the reaction mixture remains below about 150° C. during the combination of reactants in step (a).

17. A process according to claim 16 wherein the halogeno-nitrophenyl compound comprises para-chloro-nitrobenzene.

18. A process according to claim 16 wherein said base comprises an alkali metal hydroxide.

19. A process according to claim 18 wherein the molar ratio of halogeno-nitrophenyl compound to base is at least 1.15:1.

20. A process according to claim 16 wherein step (a) is performed at a temperature in the range of about 115° to 130° C.

21. A process according to claim 20 wherein step (b) is performed at a temperature in the range of about 160° to 176° C.

22. A process according to claim 16 wherein a hydrocarbon entrainer is added to the reaction mixture and the water is continously removed from the reaction system by the heteroazeotropic distillation of water with said entrainer which is comprised of a hydrocarbon which is liquid at room temperature and has a boiling point less than about 200° C.

23. A process according to claim 16 wherein the reaction is conducted in a reaction medium comprising an organic solvent capable of dissolving the halogenonitrophenyl compound.

24. A process according to claim 23 wherein the reaction is conducted in dimethyl sulfoxide as said solvent.

25. A process according to claim 23 wherein, after the reaction is completed, the di(nitrophenyl) ether is recovered from the reaction product mixture by:
  (1) separating said solvent and unreacted halogenonitrophenyl compound from said mixture by vacuum distillation,
  (2) treating the residue of step (a) with a non-aqueous extracting solvent for the di(nitrophenyl) ether at a temperature at which said ether dissolves in said extracting solvent,
  (3) cooling the resulting composition to a temperature at which two separate liquid layers are formed, and
  (4) separating the ether containing layer from the resulting two-layer composition.

26. A process according to claim 25 wherein step (1) is performed at a temperature in the range of about 150° to 250° C.

27. A process according to claim 26 wherein the composition from step (2) is cooled to a temperature in the range of about 135° to 140° C.

28. A process according to claim 25 wherein said extracting solvent is an aliphatic or aromatic hydrocarbon or mixtures thereof.

29. A process according to claim 27 wherein the solvent is selected from the group consisting of decahydronaphthalene, dodecane and decane.

30. A process according to claim 28 wherein the solvent is decane.

31. A process for extracting di(nitrophenyl) ether from a reaction product mixture containing said ether which comprises:
  (a) treating said mixture with a non-aqueous extracting solvent at a temperature at which said ether dissolves in said solvent,
  (b) cooling the resulting composition to a temperature at which two separate liquid layers are formed, and
  (c) separating the ether containing layer from the resulting two-layer composition.

32. A process according to claim 30 wherein step (a) is performed at a temperature in the range of about 150° to 250° C. and step (c) is performed at a temperature in the range of about 135° to 140° C.

33. A process according to claim 30 wherein said extracting solvent is an aliphatic or aromatic hydrocarbon or mixtures thereof.

34. A process according to claim 32 wherein the solvent is selected from the group consisting of decahydronaphthalene, dodecane and decane.

35. A process according to claim 33 wherein the solvent is decane.

* * * * *